United States Patent
Braun

(10) Patent No.: US 10,017,452 B2
(45) Date of Patent: Jul. 10, 2018

(54) DISTILLATION PROCESS COMPRISING AT LEAST TWO DISTILLATION STEPS TO OBTAIN PURIFIED HALOGENATED CARBOXYLIC ACID HALIDE, AND USE OF THE PURIFIED HALOGENATED CARBOXYLIC ACID HALIDE

(71) Applicant: SOLVAY SA, Brussels (BE)

(72) Inventor: Max Josef Braun, Wedemark (DE)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 15/505,755

(22) PCT Filed: Aug. 13, 2015

(86) PCT No.: PCT/EP2015/068671
§ 371 (c)(1),
(2) Date: Feb. 22, 2017

(87) PCT Pub. No.: WO2016/026767
PCT Pub. Date: Feb. 25, 2016

(65) Prior Publication Data
US 2017/0267622 A1    Sep. 21, 2017

(30) Foreign Application Priority Data
Aug. 22, 2014 (EP) .................................... 14182035

(51) Int. Cl.
C07C 51/64    (2006.01)
(52) U.S. Cl.
CPC .................... C07C 51/64 (2013.01)

(58) Field of Classification Search
USPC ........................................................ 562/866
See application file for complete search history.

(56) References Cited

U.S. PATENT DOCUMENTS

| | | | |
|---|---|---|---|
| 2,399,641 A | 5/1946 | Kirkbride | |
| 2,862,964 A * | 12/1958 | Lacey | ..................... C07C 51/00 562/858 |
| 4,141,895 A | 2/1979 | Middleton | |
| 4,374,782 A | 2/1983 | Anello et al. | |
| 4,643,851 A | 2/1987 | Cheminal et al. | |
| 5,241,113 A | 8/1993 | Jacobson | |
| 5,545,298 A | 8/1996 | Braun et al. | |
| 5,569,782 A | 10/1996 | Braun et al. | |
| 5,659,078 A | 8/1997 | Ebmeyer et al. | |
| 6,255,524 B1 | 7/2001 | Aoyama et al. | |
| 7,358,387 B2 | 4/2008 | Lantzsch et al. | |
| 7,754,927 B2 | 7/2010 | Komata et al. | |
| 2010/0113834 A1 | 5/2010 | Komata et al. | |

FOREIGN PATENT DOCUMENTS

| | | |
|---|---|---|
| DE | 1069137 A | 11/1959 |
| EP | 0623577 A1 | 4/1994 |
| EP | 0638539 A2 | 8/1994 |
| WO | 200542468 A1 | 5/2005 |
| WO | 200664251 A1 | 6/2006 |
| WO | 20100037688 A1 | 4/2010 |
| WO | 2011003860 A1 | 1/2011 |
| WO | 201225469 A1 | 3/2012 |

* cited by examiner

*Primary Examiner* — Deborah D Carr

(57) ABSTRACT

The present invention concerns a process for the obtention of a halogenated carboxylic halide having a reduced content of impurities, a fraction of the halogenated carboxylic halide having a reduced content of impurities, and its use in the manufacture of agriculturally and pharmaceutically active compounds.

19 Claims, No Drawings

DISTILLATION PROCESS COMPRISING AT LEAST TWO DISTILLATION STEPS TO OBTAIN PURIFIED HALOGENATED CARBOXYLIC ACID HALIDE, AND USE OF THE PURIFIED HALOGENATED CARBOXYLIC ACID HALIDE

This application is a U.S. national stage entry under 35 U.S.C. § 371 of International Application No. PCT/EP2015/068671 filed Aug. 13, 2015, which claims priority to European application No. 14182035.7, filed on Aug. 22, 2014. The entire contents of these applications are explicitly incorporated herein by this reference.

The present invention concerns a process for the obtention of a fluorinated and/or chlorinated carboxylic halide having a reduced content of impurities, a fraction of the fluorinated carboxylic halide and/or chlorinated carboxylic halide having a reduced content of impurities, and its use in the manufacture of agriculturally and pharmaceutically active compounds.

Fluorinated and/or chlorinated carboxylic halides, for example trifluoroacetylchloride (TFAC), difluoroacetylchloride (DFAC) or chlorodifluoroacetylchloride (CDFAC), are valuable intermediates in chemical synthesis, for example in the preparation of herbicides, surfactants and pharmaceuticals. For example, trifluoroacetyl chloride is a starting material for the synthesis of 4-ethoxy-1,1,1-trifluoromethyl-3-buten-2-one, which can suitably be converted into cyclic intermediates for agriculturally active ingredients, see, for example WO2011/3860 and WO2010037688. CDFAC can, for example, be converted to fluorosubstituted-3-oxo-alcanoic acids, which can further be converted into intermediates for agriculturally active compounds, see for example WO2010037688 and WO2012/25469. DFAC is, for example, used for the synthesis of CDK inhibitors, as described in WO2006/64251, or agriculturally active compounds, as described, for example, in WO2005/42468.

EP0638539A describes the synthesis of fluorinated carboxylic acid chlorides with a workup which includes a low-temperature condenser at −60° C., followed by a "fine distillation" in a 40 cm packed column. The purity of the products is not reported.

DE1069137 describes the synthesis of fluorinated and chlorinated carboxylic acid chlorides, wherein the product is distilled. The examples are operated on a typical lab scale; the purity of the products is not reported.

In particular, for industrial manufacture of building blocks for agriculturally and pharmaceutically active compounds, the purity of fluorinated carboxylic acid halides is critical for the quality of downstream products, viability of apparatus, in particular in view of corrosive impurities, and waste management. There is an ongoing industrial need for a scalable process for the purification of fluorinated carboxylic halides.

In consequence, the invention concerns a process for the obtention of a compound of the formula (I) R1-C(O)X having a reduced content of impurities which comprises the steps a) subjecting a crude fraction comprising the compound of formula (I) R1-C(O)X and impurities to at least two distillation steps, wherein the at least two distillation steps are performed at different pressures. In a preferred way, a) comprises at least three distillation steps, consisting of a high pressure distillation step, a medium pressure distillation step and a low pressure distillation step carried out at different pressures.

The invention further concerns a fraction of a compound of formula (I) R1-C(O)X having a reduced content of impurities, obtainable by the said distillation process, in particular when the compound of formula (I) was manufactured by oxidation of a compound of formula (II) R1-CHX'$_2$, and the use of the fraction having a reduced content of impurities for the manufacture of a pharmaceutically or agriculturally active compounds.

Another aspect of the present invention is a process for the manufacture of agriculturally or pharmaceutically active compounds, comprising the process for the obtention of a compound of the formula (I) R1-C(O)X having a reduced content of impurities.

It has been found that a compound of the formula (I) R1-C(O)X, in particular TFAC and CDFAC, having a reduced content of impurities can advantageously be obtained by applying a distillation process comprising at least two, preferably at least three distillation steps at different pressures. The process makes it possible to achieve an efficient separation of impurities from the compound of formula (I) R1-C(O)X, in particular TFAC, DFAC and CDFAC, by a physical method. The recovered purified fraction of (I) R1-C(O)X can be used as starting material for the lab scale or industrial scale synthesis and manufacture of further compounds and building blocks, in particular for agriculturally or pharmaceutically active compounds, while having a reduced amount of impurities, which allows for reduced corrosion in apparatus and a reduced amount of impurities and waste in downstream processes. The process effectively reduces both inorganic, for example hydrogen halides, and organic impurities. Especially if hydrogen halide, in particular HCl, is present in a significant amount, the purification process also allows for the recovery of said hydrogen halide as a fraction containing hydrogen halide and a reduced amount of impurities. Such a fraction can suitably be used for downstream processes, for example in the oxychlorination of alkanes or olefins. One example of oxychlorination is the manufacture of vinylchloride from ethylene. The process according to the present invention can be carried out in an easy manner and allows for use of steam-heating/water-cooling.

In the process according to the present invention, R1 and C1 to C3 alkyl group, which is substituted by at least one fluorine and/or at least one chlorine atom. In one aspect, R1 is substituted by at least 1, preferably at least 2 fluorine atoms; for example, R1 is methyl substituted by at least fluorine atom and, and thus R1 is selected from the group consisting of $CH_2F$, $CF_2H$ and $CF_3$. In another aspect, R1 is methyl substituted by at least one fluorine and at least one chlorine atom; in this aspect, R1 is selected from the group consisting of CFClH, $CF_2Cl$ and $CFCl_2$, wherein $CF_2Cl$ is preferred. In yet another aspect, R1 is methyl substituted by at least one chlorine atom and by no other halide species, and thus R1 is selected from the group consisting of $CH_2Cl$, $CCl_2$ and $CCl_3$. R1 can further be selected from ethyl, n-propyl and i-propyl, which are substituted by at least one fluorine atom, at least one fluorine atom and at least one chlorine atom, or at least one chlorine atom. Preferred compounds of formula (I) R1-C(O)X according to this invention are trifluoroacetyl chloride (TFAC), difluoroacetyl chloride (DFAC), difluorochloroacetyl chloride (CDFAC) and trichloroacetyl chloride, with TFAC and CDFAC being the most preferred compounds. In one aspect, when R1=$CH_2Cl$, $CCl_2$ or $CCl_3$, in particular $CH_2Cl$, the process for the obtention of a compound of the formula (I) R1-C(O)X having a reduced content of impurities comprises at least three distillation steps, preferably three distillation steps, which are performed at different pressures.

Acid halides used in the present invention can be obtained, for example, by photooxidation of halogenated precursor alkanes, in particular as described in U.S. Pat. No. 5,569,782 the content of which is incorporated by reference in the present application. In particular, trifluoroacetyl chloride, which is a particularly preferred compound of formula (I) in the present invention, can be obtained by photooxidation of 1,1,1-Trifluoro-2,2-dichloroethane (HCFC-123). Other ways to manufacture acid halides of formula (I) are described, for example, in EP0623577, U.S. Pat. No. 5,545,298A, U.S. Pat. No. 4,643,851, U.S. Pat. No. 5,241,113, U.S. Pat. No. 5,659,078, U.S. Pat. No. 6,255,524 and U.S. Pat. No. 7,754,927. Generally, the purification method according to the present invention is suitable for reducing impurities in crude fractions containing a compound of formula (I) and impurities, regardless of the way how the compound according to formula (I) was produced. The manufacture of the fraction containing the compound of formula (I) and impurities by oxidation of formula (II) $R1-CHX'_2$, wherein R1 has the same definition as above, and X' is the same or different, wherein X' is a halogen selected from the group consisting of Cl, F and Br, in particular wherein X' is Cl, is particularly preferred in view of the effectiveness of the purification process according to the present invention.

According to the present invention, a crude fraction comprising the compound of formula (I) R1-C(O)X and impurities is subjected to at least two, preferably three distillation steps which are performed at different pressures. When two distillation steps are applied, these consist of a high pressure distillation step and a low pressure distillation step. In a preferred embodiment, a) comprises at least three distillation steps, which consist of a high pressure distillation step, a medium pressure distillation step and a low pressure distillation step. According to a preferred embodiment, the high pressure distillation step is performed first, the medium pressure distillation step is performed second and the low pressure distillation step is performed third. Generally, the at least two, preferably least three distillation steps can be performed in an order which is suited for the impurity profile of the crude fraction in order to obtain a fraction containing compound (I) and a reduced amount of impurities.

In the present description, any reference to the pressure corresponds to the absolute pressure, measured at the top of the distillation column.

In a preferred embodiment, three distillation steps are applied in a). Concerning the pressure values which are applied in the different distillation steps, the medium pressure distillation step is generally carried out at a pressure of at least 1 bar lower than the high pressure distillation step. Generally, the pressure difference between the high pressure distillation step and the medium pressure distillation step is from 1 to 10 bar. Often, the pressure difference between the high pressure distillation step and the medium pressure distillation step is equal to or more than 1 bar, preferably equal to or more than 2 bar and most preferably equal to or more than 3 bar. Often, the pressure difference between the high pressure distillation step and the medium pressure distillation step is equal to or less than 10 bar, preferably equal to or less than 9 bar and most preferably equal to or less than 8 bar. Generally, the pressure difference between the medium pressure distillation step and the low pressure distillation step is from 0.2 to 9 bar. Often, the pressure difference between the medium pressure distillation step and the low pressure distillation step is equal to or more than 0.2 bar, preferably equal to or more than 0.4 bar and most preferably equal to or more than 0.6 bar. Often, the pressure difference between the low pressure distillation step and the medium pressure distillation step is equal to or less than 9 bar, preferably equal to or less than 8 bar and most preferably equal to or less than 7 bar.

When three distillation steps are applied in a), generally, the pressure in the high pressure distillation step is from 12 to 18 bar. Often, the pressure in the high pressure distillation step is equal to or more than 12 bar, preferably equal to or more than 13 bar and most preferably equal to or more than 14 bar. Often, the pressure in the high pressure distillation step is equal to or lower than 18 bar, preferably equal to or lower than 17 bar and most preferably equal to or lower than 16 bar.

When three distillation steps are applied in a), generally, the pressure in the medium pressure distillation step is from 6 to 12 bar. Often, the pressure in the medium pressure distillation step is equal to or more than 6 bar, preferably equal to or more than 6.5 bar and most preferably equal to or more than 7 bar. Often, the pressure in the high pressure distillation step is equal to or lower than 12 bar, preferably equal to or lower than 11 bar and most preferably equal to or lower than 10 bar.

When three distillation steps are applied in a), generally the pressure in the low pressure distillation step is from 1 to 9 bar. Often, the pressure in the low pressure distillation step is equal to or more than 1 bar, preferably equal to or more than 1.5 bar and most preferably equal to or more than 2 bar. Often, the pressure in the low pressure distillation step is equal to or lower than 9 bar, preferably equal to or lower than 8 bar and most preferably equal to or lower than 7 bar.

In one aspect of the invention, the fraction of the compound of formula (I) having a reduced content of impurities is recovered from the low pressure distillation step as top product.

In another aspect of the invention, the fraction of the compound of formula (I) having a reduced content of impurities is recovered from the low pressure distillation step as bottom product.

In one embodiment, when three distillation steps are applied in a), the high pressure distillation step is performed at a pressure of from 14 to 16, preferably at 15 bar, the subsequent medium pressure distillation step is performed at a pressure of from 8.5 to 10.5, preferably at 9.5 bar, and the subsequent low pressure distillation step is performed at a pressure of from 2 to 4, preferably at 3 bar. In this embodiment, the fraction containing the compound of the formula (I) R1-C(O)X having a reduced content of impurities, in particular TFAC, often is recovered as head product at the top of the column operated in the low pressure distillation step.

In another embodiment, when three distillation steps are applied in a), the high pressure distillation step is performed at a pressure of from 14 to 16, preferably at 15 bar, the subsequent medium pressure distillation step is performed at a pressure of from 6 to 8, preferably at 7 bar, and the subsequent low pressure distillation step is performed at a pressure of from 5 to 7, preferably at 6 bar. In this embodiment, the fraction containing the compound of the formula (I) R1-C(O)X having a reduced content of impurities, in particular TFAC, often is recovered as bottom product in the low pressure distillation step.

The temperature at which each distillation step is operated is selected according to the impurity profile of the crude fraction containing the compound of formula (I) R1-C(O)X and impurities, and the pressures and the columns operated in each individual distillation step.

In one embodiment, the compound of formula (I) is TFAC, and the fraction containing TFAC and a reduced amount of impurities is recovered as top product in the low pressure distillation step, wherein three distillation steps are applied in a). Preferably, the TFAC is manufactured according to the process described in U.S. Pat. No. 5,569,782. In this case, the temperature at which the high pressure distillation step is performed is from 50 to 80° C.; often, the temperature is equal to or higher than 50° C., preferably, the temperature is equal to or higher than 53° C., and most preferably the temperature is equal to or higher than 56° C. In this embodiment, often, the temperature is equal to or lower than 80° C., preferably, the temperature is equal to or lower than 75° C., and most preferably the temperature is equal to or lower than 70° C. In a preferred aspect of this embodiment, the temperature at the high pressure distillation step is from 60 to 68° C. Often, the distillates are collected at the top of the distillation column of the high pressure distillation step in a cooled apparatus, for example at a temperature of equal to or less than −10° C., preferably at a temperature of equal to or less than −20° C. As described above, in one embodiment, the fraction containing the compound of formula (I) and a reduced amount of impurities is collected as top product of the medium distillation step. According to this embodiment, the temperature at which the medium pressure distillation step is performed is from 50 to 80° C.; often, the temperature is equal to or higher than 50° C., preferably, the temperature is equal to or higher than 53° C., and most preferably the temperature is equal to or higher than 56° C. In this embodiment, often, the temperature is equal to or lower than 80° C., preferably, the temperature is equal to or lower than 75° C., and most preferably the temperature is equal to or lower than 70° C. Further, according to this embodiment, the temperature at which the low pressure distillation step is performed is from 60 to 110° C.; often, the temperature is equal to or higher than 60° C., preferably, the temperature is equal to or higher than 65° C., and most preferably the temperature is equal to or higher than 70° C. In this embodiment, often, the temperature in the low pressure distillation step is equal to or lower than 110° C., preferably, the temperature is equal to or lower than 100° C., and most preferably the temperature is equal to or lower than 95° C. In a preferred aspect of this embodiment, the temperature in the low pressure distillation step is from 75 to 90° C.

In another embodiment, the fraction containing the compound of formula (I) and a reduced amount of impurities is recovered as bottom product of the low pressure distillation step, wherein three distillation steps are applied in a). This is particularly useful if the compound of formula (I) is TFAC and manufactured according to a photooxidation described in U.S. Pat. No. 5,569,782, and, surprisingly, the amount of impurities in the fraction containing TFAC is even further reduced compared to that of the previous embodiment wherein the fraction containing TFAC and a reduced amount of impurities is recovered as top product. According to this embodiment, the temperature at which the medium pressure distillation step is performed is from 90 to 115° C.; often, the temperature is equal to or higher than 90° C., preferably, the temperature is equal to or higher than 94° C., and most preferably the temperature is equal to or higher than 98° C. In this embodiment, often, the temperature is equal to or lower than 115° C., preferably, the temperature is equal to or lower than 111° C., and most preferably the temperature is equal to or lower than 107° C. In a preferred aspect of this embodiment, the temperature in the medium pressure distillation step is from 100 to 106° C. In another aspect of this embodiment, the temperature in the low pressure distillation step is from 25 to 55° C. Often, the temperature in the low pressure distillation step is equal to or higher than 25° C., preferably, the temperature is equal to or higher than 30° C., and most preferably the temperature is equal to or higher than 35° C. In this embodiment, often, the temperature in the low pressure distillation step is equal to or lower than 55° C., preferably, the temperature is equal to or lower than 50° C., and most preferably the temperature is equal to or lower than 45° C. In a preferred aspect of this embodiment, the temperature in the low pressure distillation step is from 36 to 40° C.

Generally, each of the at least two, preferably three distillation steps of a) according to the present invention can be carried out in one or more distillation columns. Use will preferably be made of a single column per distillation step.

The distillation columns which can be used in the process according to the invention are known per se. Use may be made, for example, of conventional plate columns or plate columns of dual-flow type or alternatively of columns with bulk or structured packing. The number of theoretical plates in the high pressure distillation is generally at least 10. It is often at least 20. A number of at least 35 gives good results.

The number of theoretical plates in the low pressure distallation is generally at least 5. It is often at least 15. A number of at least 30 gives good results.

The number of theoretical plates in the medium pressure distallation is generally at least 6. It is often at least 16. A number of at least 31 gives good results.

The mass reboiling ratio in the high pressure distillation is generally at least 1. Frequently, the mass reboiling ratio is at least 3. More frequently, the mass reboiling ratio is at least 8. A mass reboiling ratio of at least 10 is preferred.

The mass reboiling ratio in the high pressure distillation is generally at most 100. Frequently, the mass reboiling ratio is at most 50. More frequently, the mass reboiling ratio is at most 30. A mass reboiling ratio of at most 25 is preferred.

The mass reflux ratio in the low pressure distillation is generally at least 2. Frequently, the mass reflux ratio is at least 4. A mass reflux ratio of at least 5 is preferred. The mass reflux ratio in the low pressure column is generally at most 50. Frequently, the mass reflux ratio is at most 30. A mass reflux ratio of at most 20 is preferred.

The mass reflux ratio in the medium pressure distillation is generally at least 30%. Frequently, the mass reflux ratio is at least 50%. A mass reflux ratio of at least 70% is preferred. The mass reflux ratio in the low pressure column is generally at most 40%. Frequently, the mass reflux ratio is at most 50%. A mass reflux ratio of at most 60% is preferred.

The each distillation step according to the present invention can be operated in continuous or discontinuous mode.

In one embodiment of the present invention, the crude fraction of the compound of formula (I) has been obtained by an oxidation process starting from a compound of formula (II) R1-CHX'$_2$, wherein X' is the same or different, wherein X' is a halogen selected from the group consisting of Cl, F and Br, in particular wherein X' is Cl, and wherein R1 has the same definition as above. In one preferred aspect of this embodiment, the oxidation process is a photooxidation process in the presence of oxygen, in particular wherein said photooxidation is further carried out in the presence of added elemental chlorine. A photooxidation according to this embodiment is particularly advantageous when a Hg high-pressure lamp doped with a metal iodide is used as a source for the activating radiation, in particular wherein the metal iodide is selected from the group consisting of gallium iodide, thallium iodide or cadmium iodide. Details of such a process are described in EP0638539A, which is incorporated hereby in its entirety.

In one aspect of the present invention, the crude fraction of the compound of formula (I) further contains a significant amount of HX', wherein X' is defined as above, in particular HCl, which was formed in the manufacturing process of preparing the compound of formula (I). This is particularly the case if the compound of formula (I) was prepared from the compound of formula (II) in an oxidation process, in particular a photooxidation in the presence of oxygen and elemental chlorine, such as described in EP0638539A. The purification process according to the present invention allows in the case that, if a significant amount of HX' is present in the crude fraction containing the compound of formula (I), a fraction of HX', in particular HCl having a reduced content of impurities is recovered as product stream in one or more of the distillation steps. Preferably, the fraction of HX', in particular HCl, having a reduced content of impurities, is withdrawn as top product at the top of the high pressure distillation step. The term <<significant amount of HX'>> is intended to denote an HX' content in the crude fraction containing formula (I) of from 2 to 50 weight %. Often, the HX' content in the crude fraction is equal to or more than 2 weight %, more preferably equal to or more than 10 weight %, and even more preferably equal to or more than 13 weight %. Often, the HX' content in the crude fraction is equal to or less than 50 weight %, more preferably equal to or more than 40 weight %, and even more preferably equal to or more than 30 weight %. In a most preferred way, the HX' content in the crude fraction containing formula (I) is from 15 to 20 weight %. In a preferred aspect, the HX' is HCl, and is recovered as top product in a high pressure distillation step at a pressure of from 14 to 16 bar, and trapped in a −20° C. cooling apparatus. The recovered fraction of HCl has a purity of at least 95 weight %, more preferably 96 weight %, and most preferably of at least 98 weight %.

In a most preferred embodiment of the present invention, TFAC is manufactured from 123 (1,1-dichloro-2,2,2-trifluoroethane) by photooxidation in the presence of $O_2$ and $Cl_2$ as described in EP0638539A and subjected to three distillation steps in a). The content of organic by-products generated in this reaction, namely $COCl_2$, $COF_2$ and 113a (1-chloro-2,2,2-trifluoroethane), as well as remaining staring material 123 can effectively be reduced, as well as the inorganic byproduct HCl and starting material $Cl_2$. In one aspect of this embodiment, $Cl_2$ is contained in a fraction also containing TFAC in a fraction recovered as top product from the low pressure distillation, in which the fraction containing TFAC and reduced amount of impurities is recovered as bottom product of the low pressure distillation step. The $Cl_2$/TFAC mixture can be recycled to the photooxidation step.

The present invention also concerns a fraction of a compound of formula (I) R1-C(O)X having a reduced content of impurities, obtainable by the process according the present invention, in particular when the compound of formula (I) was manufactured by oxidation of a compound of formula (II), preferably wherein the compound of formula (I) is selected from the group consisting of trifluoroacetyl chloride, difluoroacetyl chloride and difluorochloroacetyl chloride. In one preferred aspect of this embodiment, the compound of formula (I) is TFAC made by photooxidation of 123 as described in EP0638539A. In the case that the fraction containing TFAC is recovered as bottom product from the low pressure distillation step, wherein three distillation steps are performed in a), the content of fluoride in the recovered fraction is very low. Often, the fluoride ($F^-$)-content is lower than 50 ppm. Preferably, the fluoride ($F^-$)-content is lower than 30 ppm, and more preferably, the fluoride ($F^-$)-content is lower than 10 ppm. In the case that the fraction containing TFAC is recovered as top product from the low pressure distillation step, the content of fluoride in the recovered fraction is low. Often, the fluoride ($F^-$)-content is lower than 150 ppm. Preferably, the fluoride ($F^-$)-content is lower than 120 ppm, and more preferably, the fluoride ($F^-$)-content is lower than 100 ppm. In a most preferred aspect, the fluoride ($F^-$)-content is lower than 40 ppm. The ($F^-$)-content achieved by this method is often higher than 5 ppm; generally ($F^-$)-contents of from 5 to 90 ppm can be achieved. The ($F^-$)-content is suitably determined by ion chormatography of a hydrolyzed sample. Further, the fraction containing TFAC and a reduced amount of impurities usually contains from 0 to 400 ppm, preferably from 0 to 300 ppm, and more preferably from 0 to 250 ppm of 123. Most preferably, the 123 content is below 100 ppm. The 123 content is suitably determined by GC. The fraction containing TFAC and a reduced amount of impurities usually contains from 0 to 30, preferably from 0 to 20, and most preferably from 0 to 15 ppm of $Cl_2$. The $Cl_2$ content is suitably determined by ion chormatography of a hydrolyzed sample. The fraction containing TFAC and a reduced amount of impurities usually contains from 0 to 2%, preferably from 0 to 1%, and more preferably from 0 to 0.5% of HCl. Most preferably, the HCl content is below 0.01%. The HCl content is suitably determined by ion chormatography of a hydrolyzed sample. The fraction containing TFAC and a reduced amount of impurities usually contains from 0 to 0.2% preferably from 0 to 0.1%, and more preferably from 0 to 0.05% of $COCl_2$. Most preferably, the $COCl_2$ content is below 0.01%. The fraction containing TFAC and a reduced amount of impurities usually contains from 0 to 0.2% preferably from 0 to 0.1% and more preferably from 0 to 0.05% of $COF_2$. Most preferably, the $COF_2$ content is below 0.01%. The fraction containing TFAC and a reduced amount of impurities usually contains from 0 to 0.5% preferably from 0 to 0.2% and most preferably from 0 to 0.1% of 113a. The content of $COCl_2$, $COF_2$ and 113a is suitable detected by GC.

The fraction of the compound of formula (I) R1-C(O)X having a reduced content of impurities, in particular if (I) is TFAC, CDFAC or DFAC, can be used in the manufacture of agriculturally or pharmaceutically active compounds. The methods how the fractions recovered by the present invention can further be utilized as starting material for the manufacture of agriculturally or pharmaceutically active compounds can be found, for example, in the publications mentioned above.

The invention also concerns a process for the manufacture of agriculturally or pharmaceutically active compounds, comprising the process according to the present invention. Downstream process steps for the further manufacture of active ingredients or intermediates thereof benefit very much from the purity of the obtained fractions of the compounds of formula (I), as less byproducts, less waste, higher selectivity and lower corrosion of apparatus can be realized in downstream processes. The processes in which the fractions recovered by the present invention can further be utilized as starting material for the manufacture of agriculturally or pharmaceutically active compounds can be found, for example, in the publications mentioned above.

The examples which follow are intended to illustrate the present invention without, however, limiting the scope thereof.

Should the disclosure of any patents, patent applications, and publications which are incorporated herein by reference conflict with the description of the present application to the extent that it may render a term unclear, the present description shall take precedence.

EXAMPLES

Manufacture of TFAC

TFAC is manufactured according to the process described in EP0638539A and the crude product is used as crude fraction containing TFAC and impurities to be subjected to the three-step distillation process.

Example 1

The fraction containing TFAC and impurities was pressurized at 15 bar and submitted to a first distillation column (DN 50, ceramic fillers with 1 cm diameter, height 6 meters, material: Inox 1.4571 steel). The sump was kept at 63° C.; at the top of the first distillation column, a fraction containing mainly HCl was recovered by trapping at −20° C. The sump contained mainly TFAC, 123, $Cl_2$ and $COCl_2$. The sump was then submitted to a second distillation (column DN 50, ceramic fillers with 1 cm diameter, height 6 meters, material: Inox 1.4571 steel) at 9.5 bar. The sump was kept at 63° C., at the top of the column, a fraction containing mainly $Cl_2$ and a minor fraction of $COCl_2$, at 53° C. was recovered. The sump of this second distillation was then submitted to a third distillation (column DN 50, ceramic fillers with 1 cm diameter, height 6 meters, material: Inox 1.4571 steel) at 3 bar, where at the top (at 18° C., sump 84° C.) the fraction containing TFAC and a reduced amount of impurities was recovered.

Example 2

The fraction containing TFAC and impurities was pressurized at 15 bar and submitted to a first distillation column (DN 50, ceramic fillers with 1 cm diameter, height 6 meters, material: Inox 1.4571 steel). The sump was kept at 63° C.; at the top of the first distillation column, a fraction containing mainly HCl was recovered by trapping at −20° C. The sump contained mainly TFAC, 123, $Cl_2$ and $COCl_2$. The sump was then submitted to a second distillation (column DN 50, ceramic fillers with 1 cm diameter, height 6 meters, material: Inox 1.4571 steel) at 7 bar. The sump was kept at 104° C., at the top of the column, a fraction containing mainly TFAC and $Cl_2$ at 40° C. is recovered. The sump of this second distillation was then submitted to a third distillation (column DN 50, ceramic fillers with 1 cm diameter, height 6 meters, material: Inox 1.4571 steel) at 6 bar, where at the top (at 20° C.) a fraction containing mainly TFAC and $Cl_2$ was distilled of. The bottom (sump) of this third distillation was recovered as the fraction containing TFAC and a reduced amount of impurities.

TABLE I

| | Contents in weight %/ppm | | |
|---|---|---|---|
| | Crude Fraction | Example 1 Recovered TFAC product fraction (top product) | Example 2 Recovered TFAC product fraction (bottom product) |
| TFAC | 69.17% | >99% | 99.5% |
| HCl | 18.53% | <1% | <10 ppm |
| $COCl_2$ | 0.1% | 0.1 | <10 ppm |
| $COF_2$ | 0.1% | 0.1 | <10 ppm |
| 123 | 0.33% | 0% | 40 ppm |
| $Cl_2$ | 10% | <10 ppm | <10 ppm |
| $F^-$ | 4000 ppm | 500 ppm | <10 ppm |

The invention claimed is:

1. A process for the obtention of a compound of the formula (I) R1-C(O)X having a reduced content of impurities, wherein R1 is a fluorinated and/or chlorinated C1-C3 alkyl and X is a halogen, wherein the process comprises a) subjecting a crude fraction comprising compound of formula (I) R1-C(O)X and impurities to at least three distillation steps, which consist of a high pressure distillation step, a medium pressure distillation step and a low pressure distillation step and b) recovering at least a fraction of the compound of the formula (I) having a reduced content of impurities.

2. The process according to claim 1, wherein the medium pressure distillation step is carried out at a pressure of at least 1 bar lower than the high pressure distillation step, and the low pressure distillation step is carried out at a pressure of at least 0.2 bar lower than the medium pressure distillation step.

3. The process according to claim 1, wherein R1 is selected from the group consisting fluorinated and/or chlorinated methyl and fluorinated and/or chlorinated ethyl.

4. The process according to claim 1, wherein R1 is selected from the group consisting of $CF_3$, $CClF_2$, $CCl_2F$, $CHF_2$, $CHClF$, $CH_2Cl$ and $CCl_2H$.

5. The process according to claim 1, wherein X is selected from the group consisting of Cl, F and Br.

6. The process according to claim 1, wherein the compound of formula (I) is selected from the group consisting of trifluoroacetyl chloride, difluoroacetyl chloride and difluorochloroacetyl chloride.

7. The process according to claim 1, wherein the pressure difference between the high pressure distillation step and the medium pressure distillation step is from 1 to 10 bar, and wherein the pressure difference between the medium pressure distillation step and the low pressure distillation step is from 1 to 8 bar.

8. The process according to claim 1, wherein the pressure in the high pressure distillation step is from 12 to 18 bar, the pressure in the medium pressure distillation step is from 6 to 12 bar, and the pressure in the low pressure distillation step is from 1 to 9 bar.

9. The process according to claim 1, wherein the high pressure distillation step is performed first, the medium pressure distillation step is performed second and the low pressure distillation step is performed third.

10. The process according to claim 1, wherein the fraction of the compound of formula (I) having a reduced content of impurities is recovered from the low pressure distillation step as top product.

11. The process according to claim 1, wherein the fraction of the compound of formula (I) having a reduced content of impurities is recovered from the low pressure distillation step as bottom product.

12. The process according to claim 1, wherein the crude fraction of the compound of formula (I) has been obtained by an oxidation process starting from a compound of formula (II) R1-CHX'$_2$, wherein each X' is the same or different, wherein X' is a halogen selected from the group consisting of Cl, F and Br, and wherein R1 is a fluorinated and/or chlorinated C1-C3 alkyl.

13. The process according to claim 1, wherein the crude fraction comprising the compound of formula (I) R1-C(O)X and impurities contains HX, and wherein a fraction of HX having a reduced content of impurities is recovered, wherein X is a halogen.

14. A fraction of a compound of formula (I) R1-C(O)X having a reduced content of impurities, obtainable by the process according to claim 1.

15. A process for the manufacture of agriculturally or pharmaceutically active compounds, comprising the process according to claim 1.

16. The process according to claim 5, wherein X is Cl.

17. The process according to claim 12, wherein each X' is Cl.

18. A fraction of a compound of formula (I) R1-C(O)X having a reduced content of impurities, obtainable by the process according to claim 12.

19. The fraction according to claim 18, wherein the compound of formula (I) is selected from the group consisting of trifluoroacetyl chloride, difluoroacetyl chloride and difluorochloroacetyl chloride.

* * * * *